(12) United States Patent
Mitani et al.

(10) Patent No.: US 8,425,405 B2
(45) Date of Patent: Apr. 23, 2013

(54) ELECTRONIC ENDOSCOPE APPARATUS

(75) Inventors: Takahiko Mitani, Hachioji (JP); Akira Muramatsu, Hachioji (JP); Seiji Sakai, Chofu (JP); Tomoaki Yamashita, Tokyo (JP); Masahiro Kawauchi, Fuchu (JP); Yuichi Wataya, Akiruno (JP)

(73) Assignee: Olympus Medical Systems Corp., Tokyo (JP)

(*) Notice: Subject to any disclaimer, the term of this patent is extended or adjusted under 35 U.S.C. 154(b) by 597 days.

(21) Appl. No.: 12/432,053

(22) Filed: Apr. 29, 2009

(65) Prior Publication Data

US 2009/0292169 A1    Nov. 26, 2009

(30) Foreign Application Priority Data

May 21, 2008   (JP) ................................. 2008-133488

(51) Int. Cl.
 *A61B 1/04*   (2006.01)
 *A61B 1/00*   (2006.01)
(52) U.S. Cl.
 USPC ............. 600/110; 600/130; 600/134; 348/72; 348/65
(58) Field of Classification Search .................. 600/110, 600/117, 118, 127, 121, 129, 109, 180, 176, 600/324, 160; 348/72, 76, 65
 See application file for complete search history.

(56) References Cited

U.S. PATENT DOCUMENTS

| | | | |
|---|---|---|---|
| 4,343,300 A * | 8/1982 | Hattori ........................... | 600/109 |
| 4,996,975 A | 3/1991 | Nakamura | |
| 5,434,615 A | 7/1995 | Matumoto | |
| 5,569,158 A * | 10/1996 | Suzuki et al. ................. | 600/110 |
| 6,491,628 B1 * | 12/2002 | Kobayashi .................... | 600/168 |
| 6,635,011 B1 * | 10/2003 | Ozawa et al. ................. | 600/178 |
| 6,697,101 B1 * | 2/2004 | Takahashi et al. ............. | 348/71 |
| 6,827,683 B2 * | 12/2004 | Otawara ........................ | 600/123 |
| 6,869,394 B2 * | 3/2005 | Ishibiki ........................ | 600/127 |

(Continued)

FOREIGN PATENT DOCUMENTS

| | | |
|---|---|---|
| EP | 1 455 216 A1 | 9/2004 |
| FR | 2 761 561 A1 | 10/1998 |

(Continued)

OTHER PUBLICATIONS

Japanese Office Action dated Jan. 22, 2013 in Japanese Patent Application No. 2008-133488.

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

An electronic endoscope apparatus includes: an image pickup apparatus mounted at a distal end portion of an insertion portion; an operation portion provided consecutively at the insertion portion, with a frame member incorporated therein; and an electrical cable extended from the operation portion for connection with an external device. In the electronic endoscope apparatus, the frame member has a circuit board portion which establishes electrical connection between shields of the insertion portion and the electrical cable, and on which various electronic parts for exchanging signals with the image pickup apparatus are mounted. In spite of the arrangement of the image pickup apparatus that can acquire high-quality images at a distal end portion of the insertion portion, a size of the apparatus, in particular, a diameter of the insertion portion, can be prevented from being increased.

9 Claims, 11 Drawing Sheets

U.S. PATENT DOCUMENTS

| | | |
|---|---|---|
| 7,355,625 B1 | 4/2008 | Mochida et al. |
| 7,365,768 B1 | 4/2008 | Ono et al. |
| 2003/0018237 A1* | 1/2003 | Okada .......................... 600/146 |
| 2008/0039689 A1* | 2/2008 | Yoshimitsu et al. .......... 600/132 |

FOREIGN PATENT DOCUMENTS

| | | |
|---|---|---|
| JP | 02 168928 A | 6/1990 |
| JP | 04-338446 A | 11/1992 |
| JP | 07-313453 A | 12/1995 |
| JP | 09-266886 A | 10/1997 |
| JP | 10-234654 | 9/1998 |
| JP | 2002-291691 A | 10/2002 |
| JP | 2005-109120 A | 4/2005 |
| JP | 2005-279299 A | 10/2005 |
| JP | 2006-15078 | 1/2006 |

* cited by examiner

ELECTRONIC ENDOSCOPE APPARATUS

This application claims benefit of Japanese Application No. 2008-133488 filed in Japan on May 21, 2008 the contents of which are incorporated by this reference.

BACKGROUND OF THE INVENTION

1. Field of the Invention

The present invention relates to an electronic endoscope apparatus having a solid-state image pickup device (charged coupled device (CCD)) at a distal end portion of the apparatus.

2. Description of the Related Art

In recent years, endoscopes have been widely used in medical and industrial fields. Mainstream endoscopes that have been used to date employ an image guide so that a user can look into an eyepiece to observe an inside of a patient's body cavity or an interior of a jet engine, for example. Also, endoscopes of recent years are incorporated with an image pickup apparatus to take images of the inside of a patient's body cavity or the interior of a jet engine, for example, to display endoscopic images on a display of an external monitor or the like.

A technique for using such an image pickup apparatus with an endoscope is disclosed, for example, in Japanese Patent Application Laid-Open Publication No. 2006-15078. Specifically, the reference suggests a medical apparatus in which a camera head incorporating a CCD is mounted on an eyepiece of a conventional endoscope, with operating switches being provided at the camera head to configure a grasping portion.

The conventional medical apparatus mentioned above uses a technique for acquiring an endoscopic image with a camera head mounted on an eyepiece of an endoscope, which is a conventional rigid endoscope having an image guide. The endoscope disclosed in the reference is a rigid endoscope having no bending portion at a distal end part thereof.

As is well known, some electronic endoscope apparatus have a soft insertion portion having a distal end part at which a CCD is arranged. Generally, endoscopes are provided with a bending portion at a distal end portion of an insertion portion and include an operation portion provided with a bending operation knob being arranged for subjecting the bending portion to bending operation.

As disclosed in Japanese Patent Application Laid-Open Publication No. 10-234654, for example, such an operation portion has an interior which is provided with a fixed board that has been obtained by injection molding of metal. The fixed board is disposed in the operation portion in order to rotatably hold a sprocket of the bending operation knob, and also to maintain predetermined rigidity of the operation portion and to retain electrical connection to the ground of the insertion portion and a universal code.

SUMMARY OF THE INVENTION

An electronic endoscope apparatus of the present invention comprises: an image pickup apparatus which is mounted on a distal end portion of an insertion portion; an operation portion which is consecutively provided at the insertion portion and incorporated with a frame member; and an electrical cable which is extended from the operation portion and connected to an external device, wherein: the frame member is provided with a circuit board portion which establishes electrical connection between shields of the insertion portion and the electrical cable, and on which various electronic parts are mounted to exchange signals with the image pickup apparatus.

The present invention configured as described above can realize an electronic endoscope apparatus which is able to prevent increase of size even when an image pickup apparatus that can acquire high-quality images is arranged at a distal end portion of an insertion portion, and in particular, prevent increase of a diameter of the insertion portion.

The above and other objects, features and advantages of the invention will become more clearly understood from the following description referring to the accompanying drawings.

DETAILED DESCRIPTION OF THE PREFERRED EMBODIMENTS

With reference to the drawings, hereinafter will be described an endoscope apparatus of the present invention.

(First Embodiment)

Figure 1:
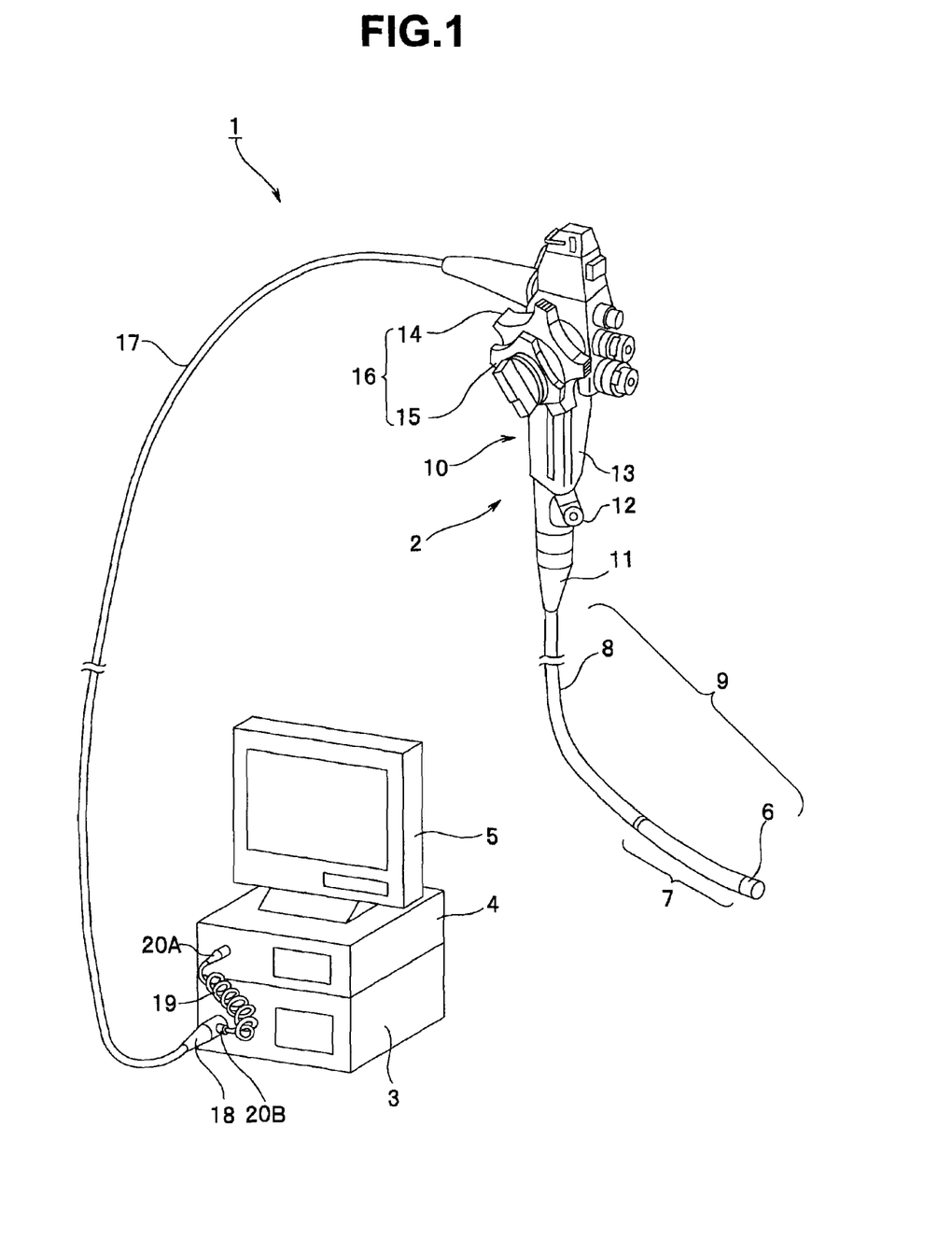
FIG. 1 is a view illustrating a configuration of an electronic endoscope system, according to a first embodiment.
Figure 2:
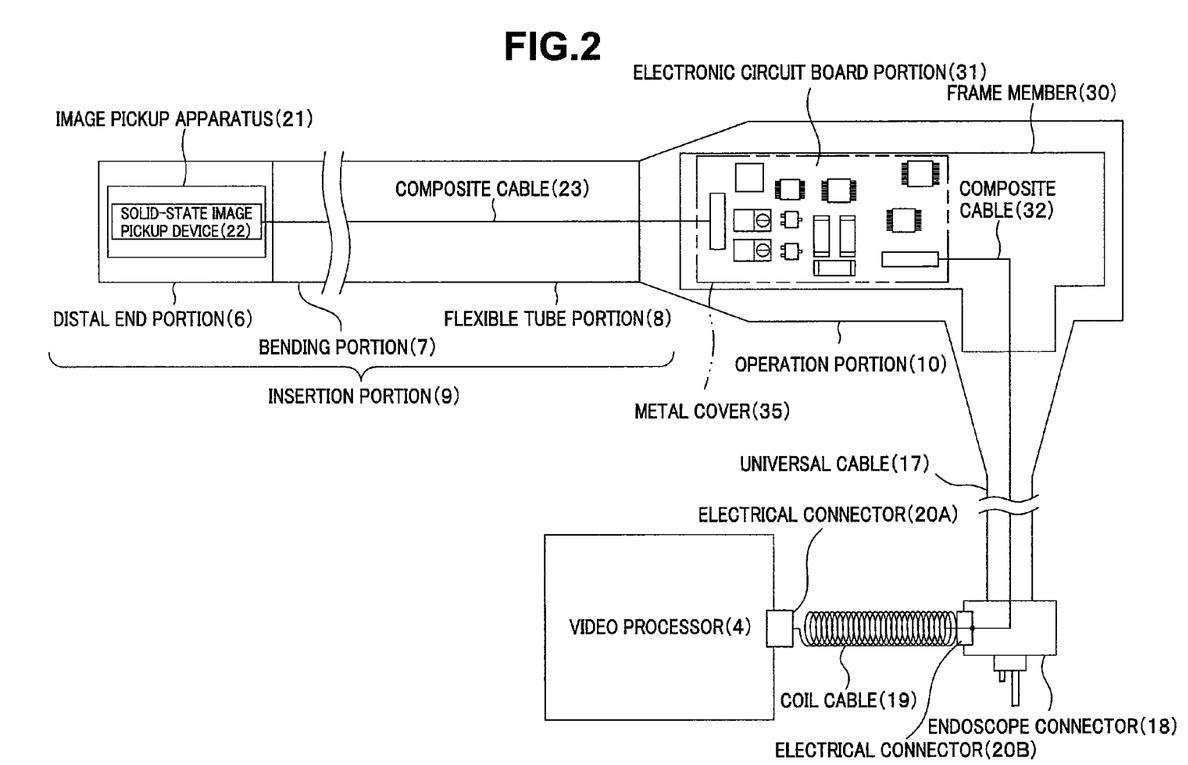
FIG. 2 is a block diagram illustrating an electrical connection configuration of the electronic endoscope system, according to the first embodiment.
Figure 3:
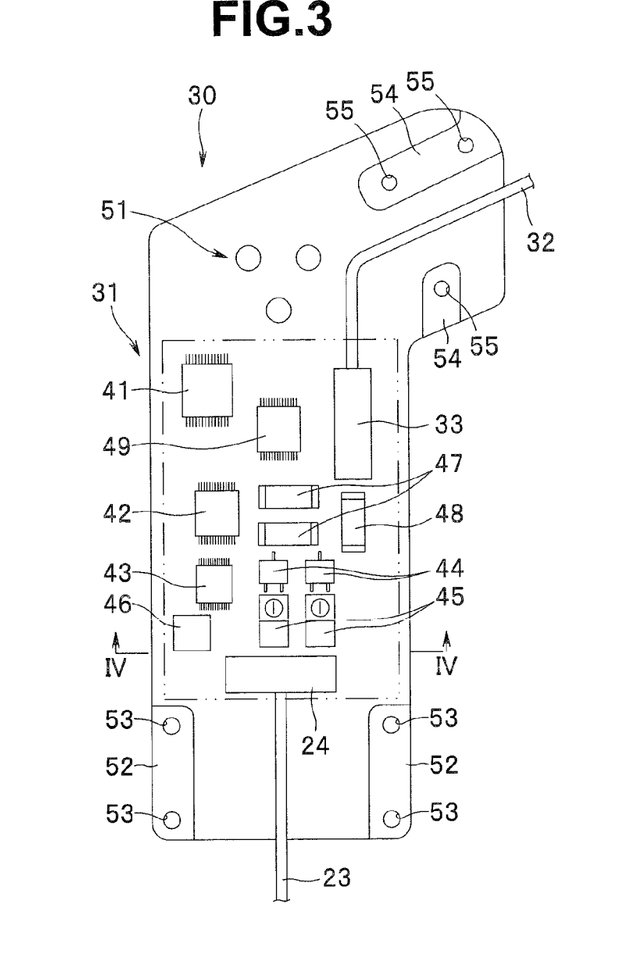
FIG. 3 is a view illustrating a configuration of an electronic circuit board, according to the first embodiment.
Figure 4:
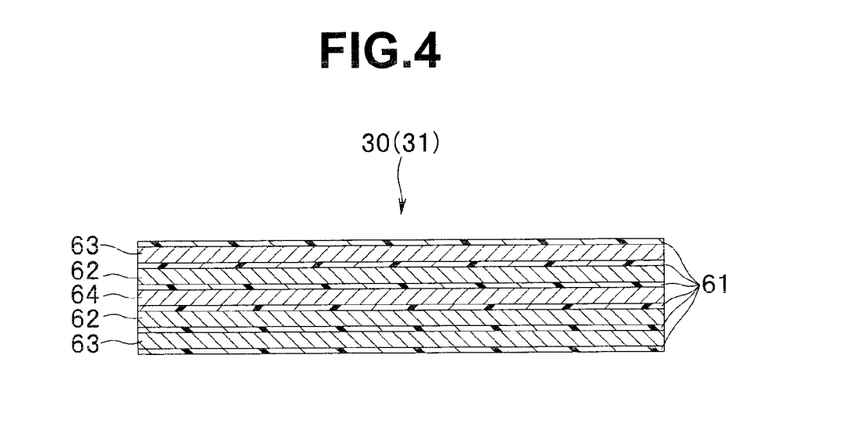
FIG. 4 is a cross-sectional view illustrating the electronic circuit board taken along IV-IV line of FIG. 3, according to the first embodiment.
Figure 5:
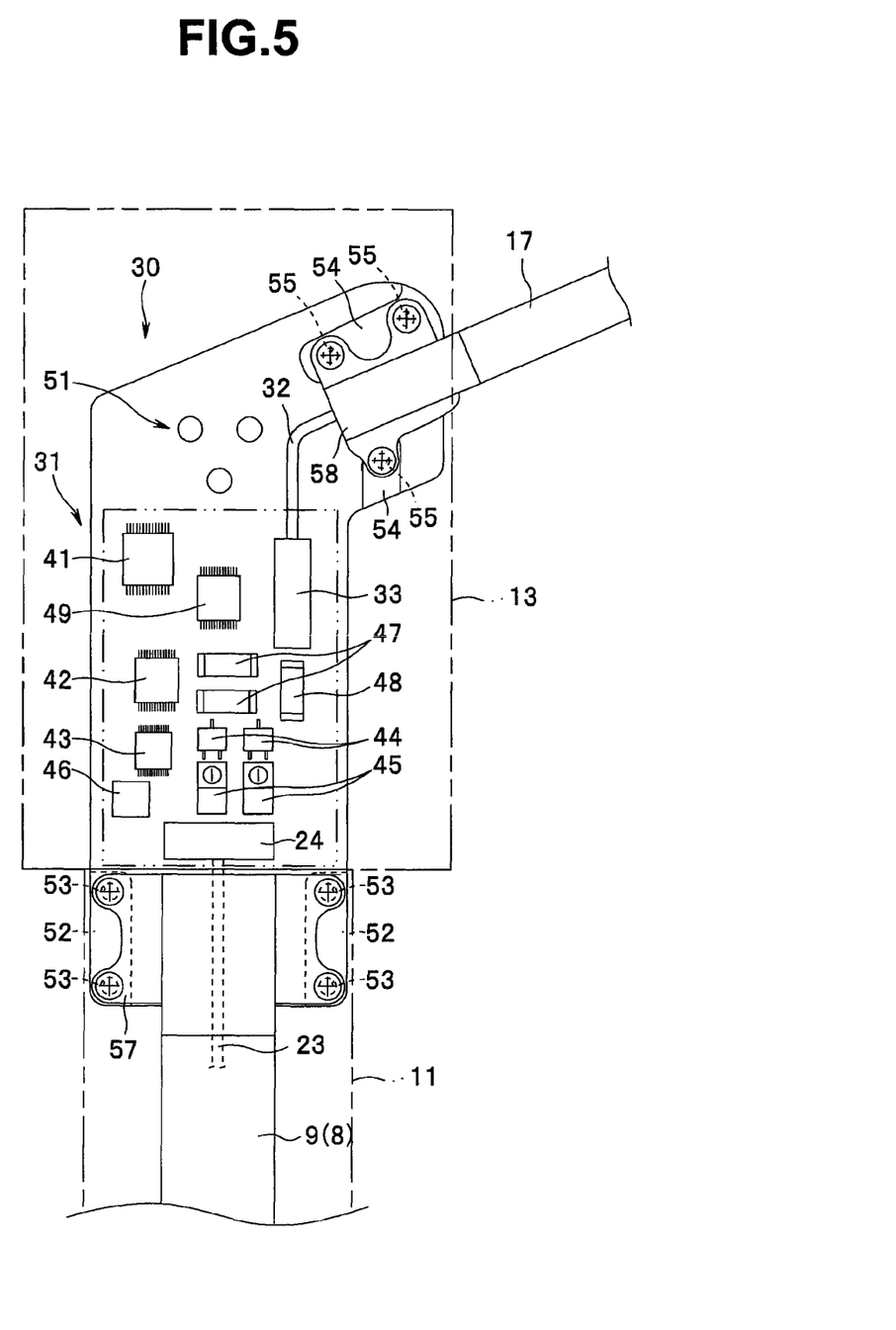
FIG. 5 is a view illustrating an electrical connection of an insertion portion and an overall shield of a universal cable, with the electronic circuit board, according to the first embodiment.
Figure 6:
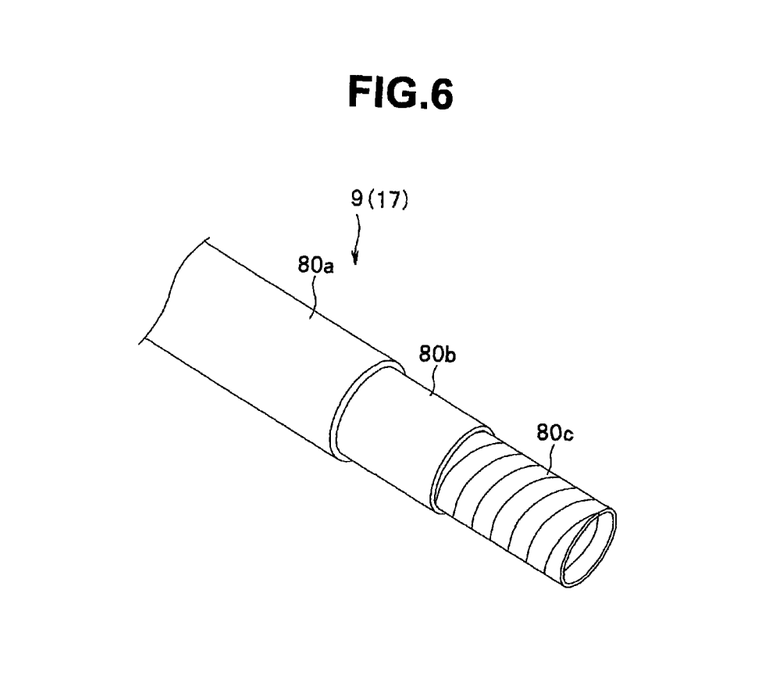
FIG. 6 is an explanatory perspective view illustrating an internal configuration of the insertion portion and the universal cable, according to the first embodiment.
Figure 7:
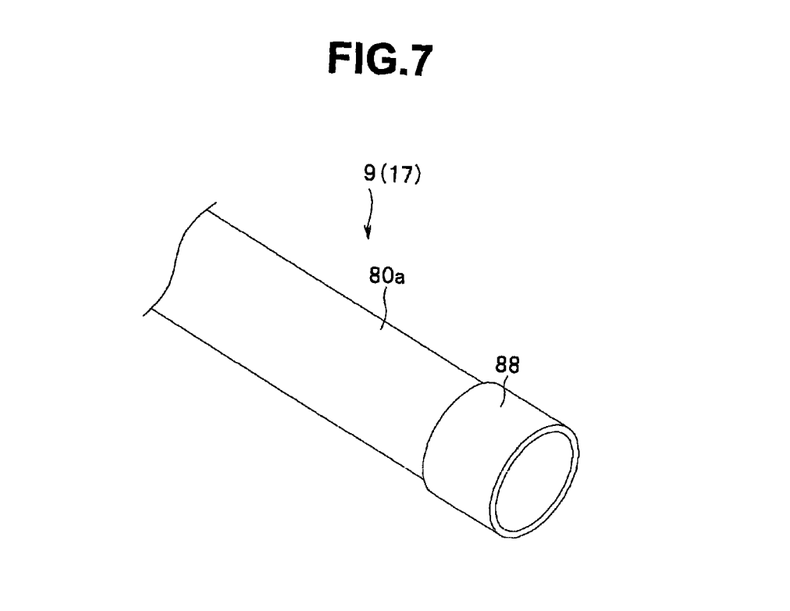
FIG. 7 is a perspective view illustrating an end portion of the insertion portion and the universal cable, according to the first embodiment.
Figure 8:
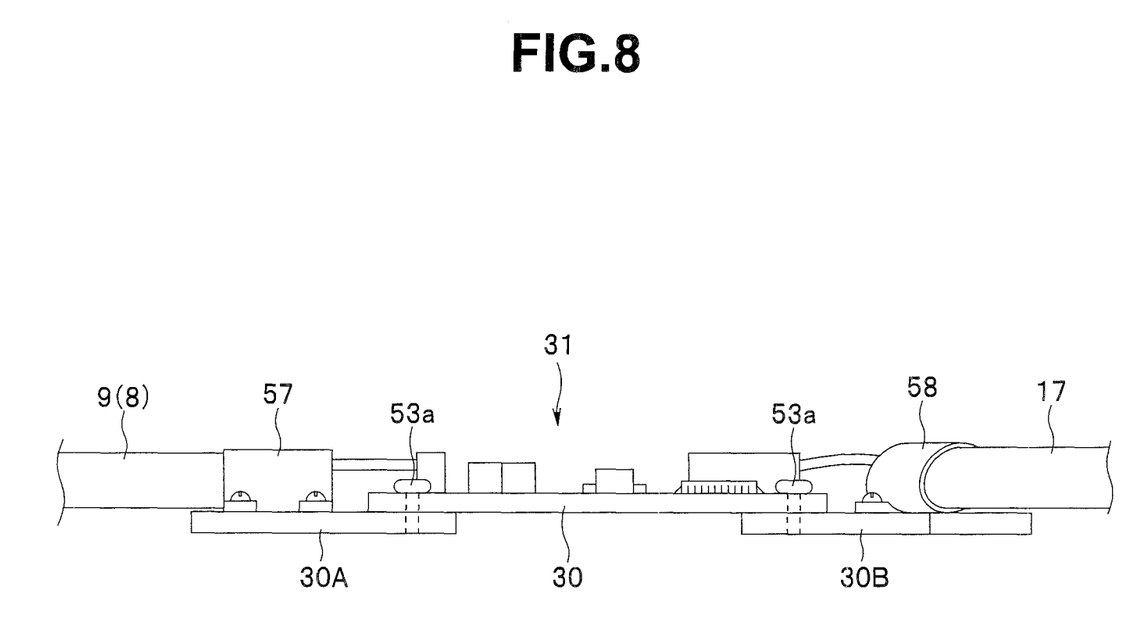
FIG. 8 is a plan view illustrating a peripheral configuration of a circuit board portion, according to a first modification.
Figure 9:
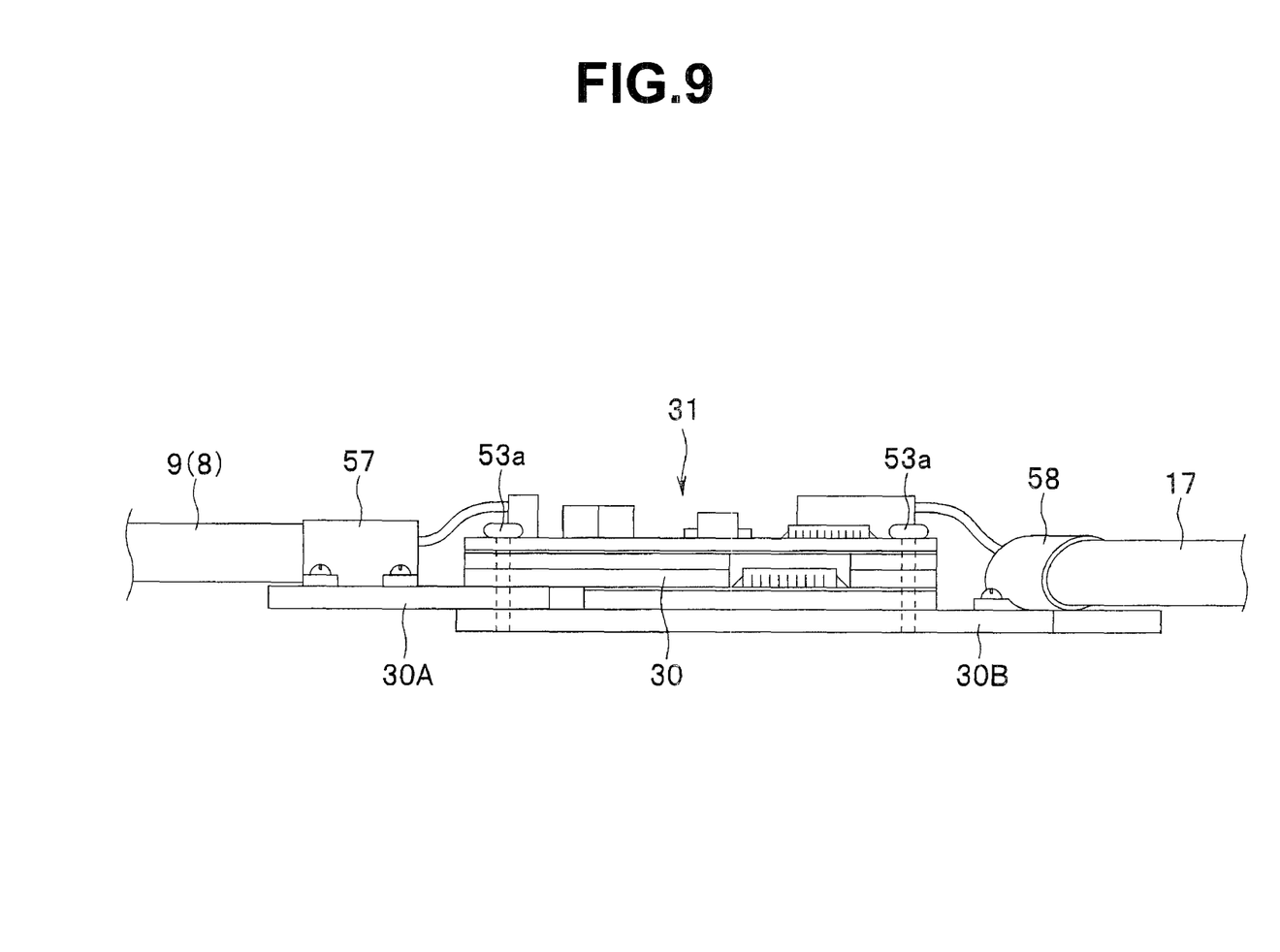
FIG. 9 is a plan view illustrating a peripheral configuration of a circuit board portion, according to a second modification.

Referring to FIGS. 1 to 5, a first embodiment of the present invention is described first. FIGS. 1 to 5 relate to the first embodiment of the present invention, in which: FIG. 1 is a view illustrating a configuration of an electronic endoscope system; FIG. 2 is a block diagram illustrating an electrical connection configuration of the electronic endoscope system; FIG. 3 is a view illustrating a configuration of an electronic circuit board; FIG. 4 is a cross-sectional view illustrating the electronic circuit board taken along IV-IV line of FIG. 3; FIG. 5 is a view illustrating an electrical connection of an insertion portion and an overall shield of a universal cable, with the electronic circuit board; FIG. 6 is an explanatory perspective view illustrating an internal configuration of the insertion portion and the universal cable; FIG. 7 is a perspective view illustrating an end portion of the insertion portion and the universal cable; FIG. 8 is a plan view illustrating a peripheral configuration of a circuit board portion according to a first modification; and FIG. 9 is a plan view illustrating a peripheral configuration of a circuit board portion according to a second modification.

As shown in FIG. 1, an electronic endoscope system 1 mainly includes an electronic endoscope apparatus 2, a light source device 3, a video processor 4 and a monitor 5.

The electronic endoscope apparatus 2 includes an elongated insertion portion 9, an operation portion 10 and a universal cable 17 which is an electrical cable. The insertion portion 9 of the electronic endoscope apparatus 2 is sequentially configured, from a distal end, by a distal end portion 6, a bending portion 7 and a flexible tube portion 8.

The operation portion 10 is connected to one end of the flexible tube portion 8 of the insertion portion 9, and includes a rear port 11, i.e. a bend preventing portion, a treatment instrument channel insertion portion 12, i.e. an opening portion of a treatment instrument channel, for inserting various treatment instruments arranged to the insertion portion 9, and an operation portion body 13.

The operation portion body 13 is rotatably arranged with a bending operation knob 16 for bending operation of the bending portion 7 of the insertion portion 9, and also arranged with switches and the like associated with various endoscopic functions. The bending operation knob 16 is arranged in such a way that a UD bending operation knob 14 for performing vertical bending operation of the bending portion 7, and an RL bending operation knob 15 for performing horizontal bending operation of the bending portion 7, are overlapped one on the other.

The universal cable 17 extended from the operation portion 10 has an extended end which is provided with an endoscope connector 18 which is detachable with the light source device 3. The electronic endoscope apparatus of the present embodiment is adapted to transmit illumination light from the light source device 3 to the distal end portion 6 by a light guide bundle. A coil cable 19 having a shape of a coil is extended from the endoscope connector 18. The coil cable 19 has an extended end which is provided with an electrical connector 20A which is detachable with the video processor 4.

The video processor 4 is electrically connected to the monitor 5 for displaying endoscopic images, and processes image pickup signals that have been subjected to photoelectric conversion by an image pickup apparatus, which will be described later, of the electronic endoscope apparatus 2. The processed signals are then outputted to the monitor 5 as image signals.

Generally, the insertion portion 9 of the electronic endoscope apparatus 2 has an entire length of about 2.5 m. The universal cable 17 connected to the electronic endoscope apparatus 2 through the operation portion 10 also has a length of about 2.5 m, with an entire length being 5.0 m or more. Further, the electronic endoscope apparatus 2 is connected to the video processor 4 through the electrical connector 20A of the coil cable 19 having a length of about 2.0 m.

Referring now to FIGS. 2 to 4, a detailed description will be provided on an electrical configuration of the electronic endoscope apparatus 2 and a circuit board portion of a frame member which is arranged in the operation portion 10.

As shown in FIG. 2, the electronic endoscope apparatus 2 of the present embodiment has the insertion portion 9 whose distal end portion 6 is incorporated with an image pickup apparatus 21 provided with a solid-state image pickup device 22, such as a CCD and CMOS. A first composite cable 23 is extended from the solid-state image pickup device 22 and inserted into the operation portion 10 for arrangement therein, through the insertion portion 9. The first composite cable 23 is made up of a bundle of plural coaxial cables and is electrically connected to a circuit board portion 31 of a frame member 30 which is arranged in the operation portion 10.

A second composite cable 32, which is inserted into the universal cable 17, is electrically connected to the circuit board portion 31. The second composite cable 32 is electrically connected to the video processor 4 through the endoscope connector 18 and through the coil cable having detachable electrical connectors 20A and 20B at both ends thereof.

The frame member 30 arranged in the operation portion 10 is provided with a metal cover 35 which covers the circuit board portion 31 to ensure noninterference property and tolerance against electromagnetic influences on electronic parts mounted on the circuit board portion 31.

As shown in FIG. 3, a plurality of electronic parts are mounted on the circuit board portion 31 of the frame member 30. The electronic parts mainly includes: an FPGA (field programmable gage array) 41, a solid-state image pickup device driver 42 and a solid-state image pickup device stabilized power source 43, which serve as input-side electronic parts for inputting signals into the solid-state image pickup device 22 through the first composite cable 23; and a plurality of, two here, transistors 44, a plurality of, two here, filters 45 and an amplifier 46, which serve as output-side electronic parts for outputting signals from the solid-state image pickup device 22 through the first composite cable 23. Other electronic parts include a resistor 47, a capacitor 48 and an LVDS (low voltage differential signaling) driver 49 which purposes, for example, stable transmission of transfer signals and noise reduction. An LVDS receiver is arranged in the video processor 4.

The circuit board portion 31 is arranged with connectors 24 and 33 which electrically connect the first and second composite cables 23 and 32, respectively, to the electronic parts, and also electrically connect grounds of coaxial lines of the composite cables 23 and 32 as well as an overall shield, to grounds, which will be described later, formed on the frame member 30.

Specifically, as shown in FIG. 4, an entirety of the frame member 30, including the circuit board portion 31, is configured by a rigid board which is made up of four ground layers 62 and 63, and a signal layer 64, with each of the layers and surfaces being ensured to be insulated by insulation layers 61. It should be noted that the frame member 30 of the present embodiment is a rigid board formed of a glass-epoxy board or a stacked ceramic board.

Of the four ground layers 62 and 63, two layers that sandwich the signal layer 64 are stacked as first ground layers 62 for shielding the coaxial lines of the composite cables 23 and 32, and two layers that are located on front and back surface sides are stacked as second ground layers 63 shielding overall the composite cables 23 and 32, the insertion portion 9 and the universal cable 17.

Further, the surface insulation layers 61 of the frame member 30 are edged and masked, for example, at four portions in front and back end surfaces to expose the second ground layers 63. The exposed second ground layers 63 can serve as fixing portions 52 and 54 to which the overall shields of the insertion portion 9 and the universal cable 17, respectively, are electrically connected.

To explain in detail, as shown in FIG. 5, two fixing portions 52 are formed in the end surfaces, on the side to which the first composite cable 23 is connected. The two fixing portions 52 are each electrically connected to the overall shield of the insertion portion 9 (flexible tube portion 8) and are formed with holes 53 for fixedly screwing the rear port 11 of the operation portion 10 and the insertion portion 9. Also, two fixing portions 54 are formed in the end surfaces, on the side to which the second composite cable 32 is connected. The two fixing portions 54 are each electrically connected to the overall shield of the universal cable 17 and are formed with holes 55 for fixedly screwing the operation portion body 13 of the operation portion 10 and the universal cable 17. The electrical connection of the insertion portion 9 and the universal cable 17 is established through bases 57 and 58, respectively, by which the overall shields are fixed to the respective end portions. The bases 57 and 58 are fixedly screwed to the corresponding fixing portions 52 and 54.

As shown in FIG. 6, each of the insertion portion 9 and the universal cable 17 is configured by inserting a braid 80b, i.e. a metal overall shield, and a metal flexible body 80c into a sheath 80a that is an outer enclosure. Essentially, the braid 80b and the metal flexible body 80c are provided for adjusting the rigidity of the insertion portion 9 and the universal cable 17, but may be utilized as electrical shields.

Therefore, as shown in FIG. 7, each of the insertion portion 9 and the universal cable 17 has an end portion which is provided with a metal annular body 88 that can be electrically connected to the braid 80b by soldering or crimping. In the operation portion 10, the metal annular body 88 is electrically connected to the circuit board portion 31. In particular, the metal annular body 88 is electrically connected to each of the bases 57 and 58 provided at respective ends of the insertion portion 9 and the universal cable 17, which ends reside on the side of the frame member 30. Thus, the braid 80b serving as an overall shield of each of the insertion portion 9 and the universal cable 17 is electrically connected to each of the bases 57 and 58 fixed to the respective end portions.

The electronic endoscope system 1 of the present embodiment configured as described above has the circuit board portion 31 arranged at the frame member 30 in the operation portion 10 of the electronic endoscope apparatus 2. The circuit board portion 31 is mounted with input/output electrical parts for exchanging electrical signals with the solid-state image pickup device 22 of the image pickup apparatus 21 which is loaded in the distal end portion 6 of the insertion portion 9. Thus, the composite cables 23 and 32 can be made thinner than conventional ones. In addition, use of the solid-state image pickup device 22 that can acquire high-quality endoscopic images of larger number of pixels than in the conventional devices, may not necessitate the use of large-diameter composite cables 23 and 32.

In other words, since the circuit board portion 31 serving as a relay circuit, is provided in the operation portion 10 of the electronic endoscope apparatus 2, a transmission path may be made shorter than in the conventional apparatus. As described above, for example, in the case of the electronic endoscope apparatus 2 having the insertion portion 9 whose entire length is about 2.5 m, the universal cable 17 whose entire length is about 2.5 m and the coil cable 19 whose entire length is about 2.0 m, the entire transmission path from the video processor 4 to the solid-state image pickup device 22 of the image pickup apparatus 21 will be about 7.0 m. In this regard, owing to the arrangement of the circuit board portion 31 serving as a relay board in the operation portion 10, an input/output transmission path to/from the solid-state image pickup device 22 will be about 2.5 m, and an input/output transmission path to/from the video processor 4 will be about 4.5 m. Thus, the transfer path can be made shorter than in the conventional cases.

Specifically, in inputting signals to the solid-state image pickup device 22 of the image pickup apparatus 21, the conventional electronic endoscope apparatus 2 had to use a driver in the video processor 4, for transmission of drive signals for driving the solid-state image pickup device 22 through a transmission path of 6.5 m, for example. Such transmission has caused drastic deterioration, such as attenuation or dullness, in the drive signals. In this regard, the electronic endoscope apparatus 2 of the present embodiment has the operation portion 10 which is provided therein with a driver for relaying drive signals for driving the solid-state image pickup device 22. Therefore, the transmission path of the drive signals for the solid-state image pickup device 22 can be shortened to 2.5 m, here, which corresponds to a path from the operation portion 10 to the solid-state image pickup device 22. Also, arranging the circuit board mounted with the driver in the operation portion 10, may contribute to mitigation of drive load, the mitigation being equal to the reduction in the length of the transmission path to 4.5 m, here, which corresponds to a path from the video processor 4 to the operation portion 10. As a result, circuits in the video processor 4 can be downsized. Further, since amplitude of the drive signals can be made small, radiation noise can be reduced.

Further, in outputting signals from the solid-state image pickup device 22, the conventional electronic endoscope apparatus 2 had to permit the video processor 4 to sample waveforms that have been dulled passing through the output-signal transmission path, which is 6.5 m long, for example, from the solid-state image pickup device 22 in the distal end portion 6. Such transmission can provide less sampling margin and thus it has been likely that the image qualities are deteriorated. In this regard, the electronic endoscope apparatus 2 of the present embodiment can mount a sampling circuit as a relay in the operation portion 10. Accordingly, the distance up to the operation portion 10, which has been 6.5 m here, can be shortened to 2.5 m here. Thus, signal transmission to the video processor 4 can be stabilized to thereby obtain good images with less signal deterioration. It should be noted that arrangement of an A/D circuit in the operation portion 10 may also enable transmission with digital signals causing less deterioration, in the downstream of the operation portion 10.

The composite cables 23 and 32 used for the electronic endoscope apparatus 2 of the present invention may be made thinner. Thinner composite cables can prevent increase of a diameter of the insertion portion 9 in the electronic endoscope apparatus 2 which is able to acquire higher-quality endoscopic images than in the conventional apparatus. In addition, as to the electronic endoscope apparatus 2 which acquires conventional-quality endoscopic images, thinner composite cables can also make a diameter of the insertion portion 9 small.

In the electronic endoscope apparatus 2, a conventionally used metal frame member incorporated in the operation portion 10 has been replaced by the frame member 30 of the present embodiment, which is in the form of a rigid stacked board. The replacement of the members, however, has not increased the size of the operation portion 10, but the size and shape of the operation portion 10 have remained substantially the same as those of the conventionally used operation portion. Thus, the electronic endoscope apparatus 2 can provide a configuration which is so convenient for female medical doctors, in particular, as to prevent deterioration in grasping properties and operability.

Further, no high-power and large-size electronic parts are required to be incorporated into the video processor 4, i.e. an external device, for exchanging electrical signals with the image pickup apparatus 21 of the electronic endoscope apparatus 2. That is, the video processor 4 can be configured by small-size electronic parts, whereby power consumption can be reduced and the size of the apparatus, per se, can be reduced.

The insertion portion 9 and the universal cable 17 may not be directly fixed to the frame member 30 of the circuit board portion 31. Alternatively, as shown in FIG. 8, metal frames 30A and 30B may be provided at both ends separately from the frame member 30, for connection with the insertion portion 9 and the universal cable 17, respectively.

Specifically, it may be so configured that the metal frames 30A and 30B are located so that edge portions thereof may overlap with respective ends of the frame member 30 so as to be fixed by fixing screws 53a. With such a configuration, strength and rigidity of the fragile frame member 30 can be compensated, which frame member 30 would otherwise be likely to be damaged by impact or the like.

Further, as shown in FIG. 9, it may be so configured that the edge portions of the metal frames 30A and 30B are located so as to be overlapped with each other. Then, the circuit board portion 31 formed of a stacked board and has a shape that matches the shape of a step formed by the metal frames 30A and 30b, may be mounted on the metal frames 30A and 30B and fixed with fixing screws 53a.

In this way, overlapping of the edge portions of the metal frames 30A and 30B can improve the strength and rigidity. At the same time, use of a stacked board as the circuit board portion 31 can increase an area for mounting electronic parts.

As described above and as shown in FIGS. 8 and 9, the electronic endoscope apparatus 2 may have a configuration in which the metal frames 30A and 30B are provided separately from the frame member 30 of the circuit board portion 31, for connection and fixation with the insertion portion 9 and the universal cable 17. Thus, strength and rigidity of the fragile frame member 30 can be compensated.

(Second Embodiment)

Figure 10:
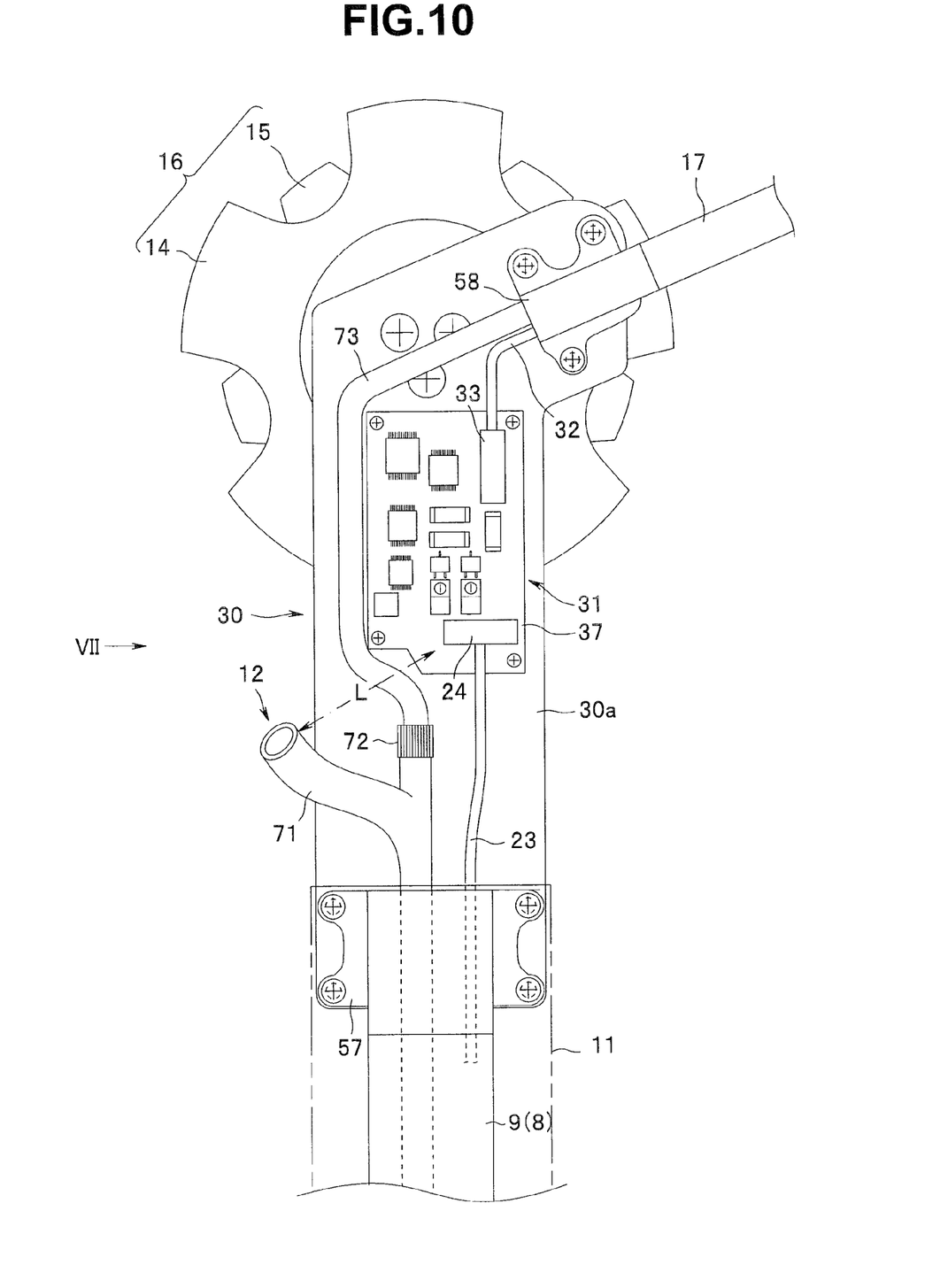
FIG. 10 is an explanatory view illustrating a positional relationship chiefly between an electronic circuit board and a treatment instrument insertion channel in an operation portion, according to a second embodiment.
Figure 11:
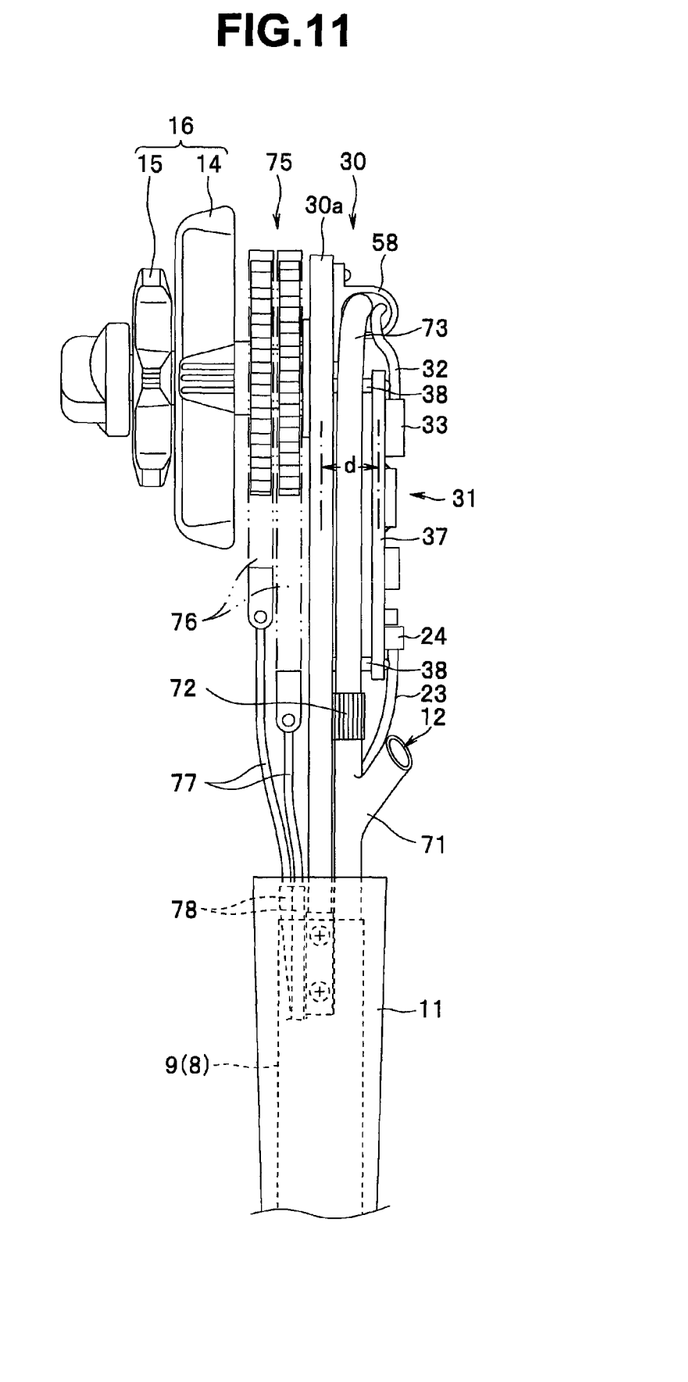
FIG. 11 is an explanatory view illustrating a positional relationship chiefly between the electronic circuit board and the treatment instrument insertion channel in the operation portion as viewed from an arrow VII of FIG. 10, according to the second embodiment.

Referring now to FIGS. 10 and 11, hereinafter is described a second embodiment of the present invention.

FIGS. 10 and 11 relate to the second embodiment of the present invention. FIG. 10 is an explanatory view illustrating a positional relationship chiefly between an electronic circuit board and a treatment instrument insertion channel in an operation portion. FIG. 11 is an explanatory view illustrating a positional relationship chiefly between the electronic circuit board and the treatment instrument insertion channel in the operation portion as viewed from an arrow VII of FIG. 10. It should be noted that, in the following description, components having the same configurations as those in the first embodiment described above are designated with the same reference symbols to omit detailed description and operational advantages of the components.

As shown in FIGS. 10 and 11, the electronic endoscope apparatus 2 of the present embodiment has the operation portion 10 which is incorporated with the frame member 30 having a frame board 30a made of metal, such as aluminum die-cast, and having the circuit board portion 31 which is provided in parallel with the frame board 30a, at a position apart from one surface of the frame board 30a by a predetermined distance "d" (see FIG. 11). The circuit board portion 31 has a rigid board 37 on which the electronic parts explained in the first embodiment are mounted.

The rigid board 37 is fixed at four corners using four leg members 38, i.e. stand spacers, so as to be parallel to the frame board 30a, being apart from the one surface of the frame board 30a by the predetermined distance "d". The distance "d" corresponds to a length of a step which is larger than a radius of a channel tube, so that runaway of the channel tube can be prevented. The four leg members 38 are adapted to fix the rigid board 37 and the frame board 30a by means of screws, for example, to establish electrical connection therebetween.

Specifically, the electronic endoscope apparatus 2 of the present embodiment has the operation portion 10 in which the frame member 30 is arranged, rotatably supporting the bending operation knob 16 and sprockets 75. In the frame member 30, the rigid board 37 of the circuit board portion 31 is provided in a space on a side opposed to the frame board 30a. Further, although not shown, top of the rigid board 37 of the circuit board portion 31 is provided with a metal cover to ensure noninterference property and tolerance against electromagnetic influences on electronic parts, as in the first embodiment.

Also, although explanation has been omitted in the first embodiment, the electronic endoscope apparatus 2 includes: a metal treatment instrument channel 71 which is arranged being inserted into the insertion portion 9; and a channel tube 73 which is connected to the channel 71 in a water-tightly communicable manner through a connecting member 72 arranged at one diverged end of the treatment instrument channel 71. The channel tube 73 is a tubular body which is obtained by guarding a soft tube with a metal coil, the soft tube being formed of PTFE. The channel tube 73 is arranged being inserted into the universal cable 17, with a rear end portion thereof being detachably connected to a suction apparatus, not shown.

The other diverged end of the treatment instrument channel 71 has an opening portion which provides a treatment instrument channel insertion portion 12 of the operation portion 10. The treatment instrument channel 71 and the channel tube 73 are arranged between the frame board 30a of the frame member 30 and the rigid board 37 of the circuit board portion 31.

The treatment instrument channel insertion portion 12 of the treatment instrument channel 71 is arranged in a direction being away from the rigid board 37. In particular, the opening of the insertion portion 12 is positioned so as to have a predetermined distance "L" from a first connector 24 which is provided at the rigid board 37 to establish electrical connection with the first composite cable 23. The distance "L" is set so that the opening will not be positioned overlapping the board, at least in the longitudinal direction of the operation portion 10.

Further, the channel tube 73 is routed for arrangement, extending from a base 58 that fixes the universal cable 17 to the frame board 30a, running along one side portion of the rigid board 37, which side is far from the base 58, and passing an area between the frame board 30a and the rigid board 37 with the distance "L" therebetween. Thus, the channel tube 73 can be efficiently and stably arranged without wobbling in the operation portion 10. Further, the channel tube 73 can be arranged at the same level as that of a position for establishing connection with the treatment instrument channel 71. Accordingly, the channel tube 73 can be prevented from being bent or being forcibly deformed.

The bending operation knob 16 (15, 14) mentioned above is arranged on the other side of the frame board 30a. The bending operation knob 16 rotatably supports the two sprockets 75 and operates the sprockets 75 so that the sprockets can be individually rotated. The sprockets 75 each engage with chains 76 whose end portions are connected with respective bending operation wires 77. The bending operation wires 77 are inserted into respective coil tubes 78 which are arranged being inserted into the insertion portion 9, for extension up to the bending portion 7.

Specifically, the two bending operation knobs 14 and 15 are configured to individually rotate/operate the respective sprockets 75. Thus, rotation of the sprocket 75 concerned may permit the chain 76 interlocked with the sprocket 75 to move. According to the amount of movement of the chain 76, the bending operation wire 77 concerned is pulled or slackened. In this way, the bending portion 7 of the insertion portion 9 is subjected to bending operation.

The electronic endoscope apparatus 2 of the present embodiment configured as described above is provided with the rigid board 37 of the circuit board portion 31 in a space in the operation portion 10. Such a configuration can exert the advantages of the first embodiment, and at the same time can also prevent increase of size of the operation portion 10.

Also, the electronic endoscope apparatus 2 may be used together with a treatment instrument, such as an electric cautery, using high frequency, which instrument is inserted into the treatment instrument channel 71 from the treatment instrument channel insertion portion 12. For this reason, in the electronic endoscope apparatus 2 of the present embodiment, the treatment instrument channel insertion portion 12 of the treatment instrument channel 71 is provided in a direction being away from the circuit board portion 31 whose shield for preventing external electrical influences has been weakened. Also, the treatment instrument channel insertion portion 12 is arranged so as to have the predetermined distance "L" from the first connector 24 for establishing electrical connection with the first composite cable 23. In this way, measures against noise are taken for the first composite cable 23, and at the same time, noninterference property and tolerance against electromagnetic influences on the circuit board portion 31 are improved. In other words, the electronic endoscope apparatus 2 of the present embodiment has a configuration with improved noninterference property and tolerance against electromagnetic influences which will be caused in the treatment using high frequency, such as by an electric cautery.

(Third Embodiment)

Referring now to FIGS. 12 to 15, hereinafter is described a third embodiment of the present invention.

Figure 12:
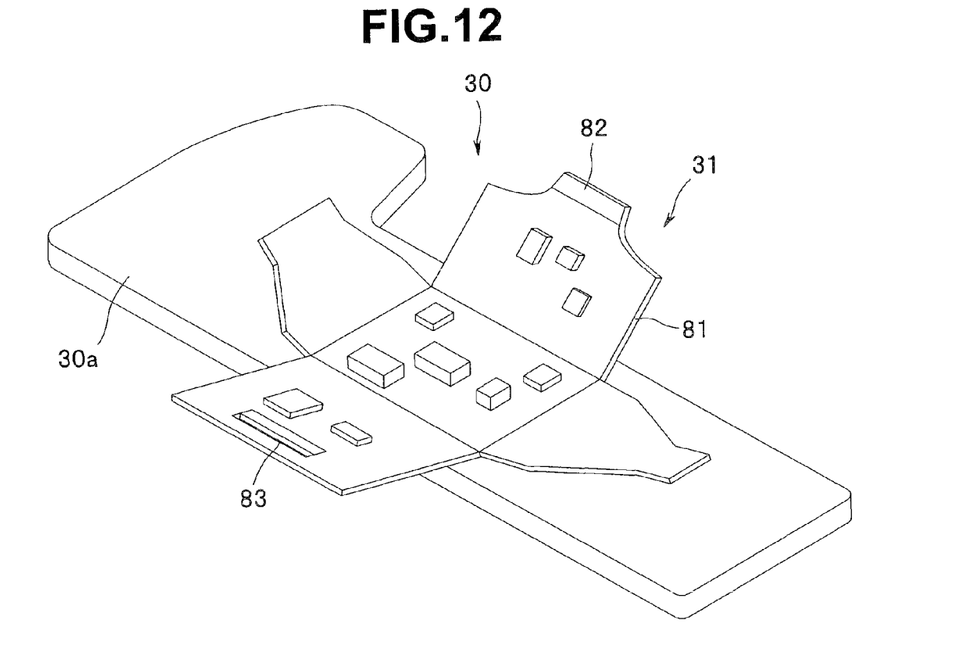
FIG. 12 is a view illustrating a circuit board portion formed of a flexible printed board on which various electronic parts are mounted, the printed board being expanded on a frame member, according to a third embodiment.
Figure 13:
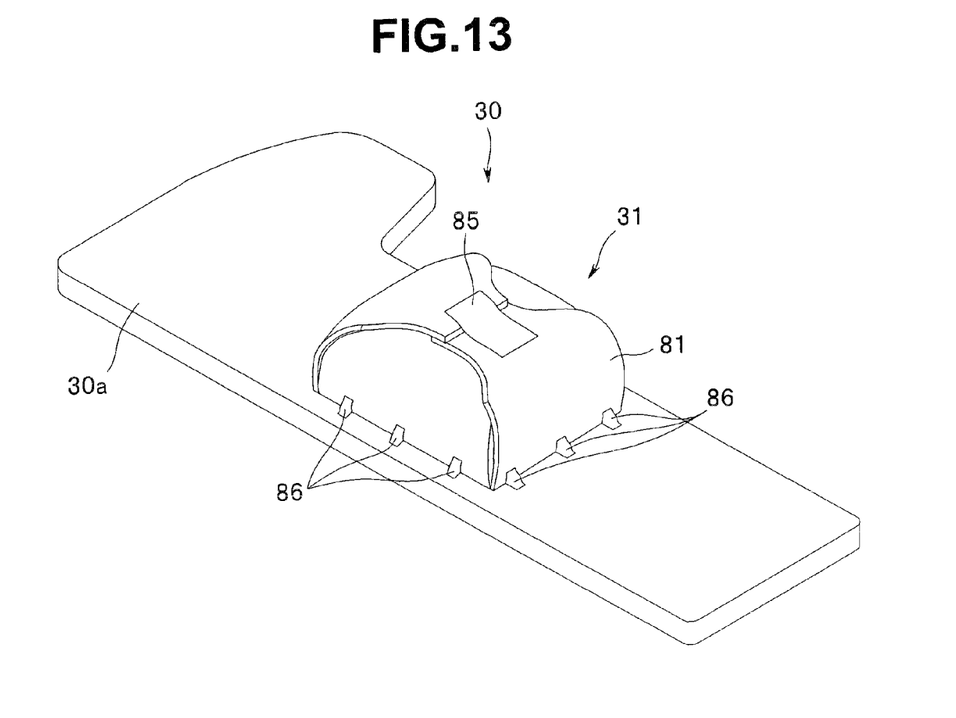
FIG. 13 is a view illustrating the circuit board portion of FIG. 12, in which the flexible printed board disposed on the frame member has been changed in shape to wrap the various electronic parts mounted on the flexible printed board, according to the third embodiment.
Figure 14:
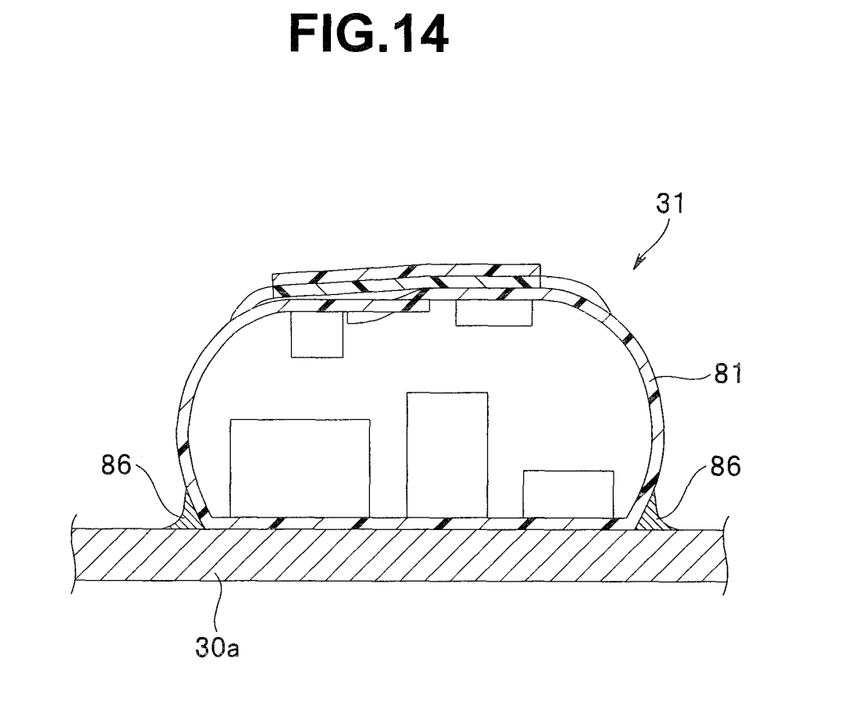
FIG. 14 is a cross-sectional view illustrating the circuit board portion disposed on the frame member, being in the state of FIG. 13, according to the third embodiment.
Figure 15:
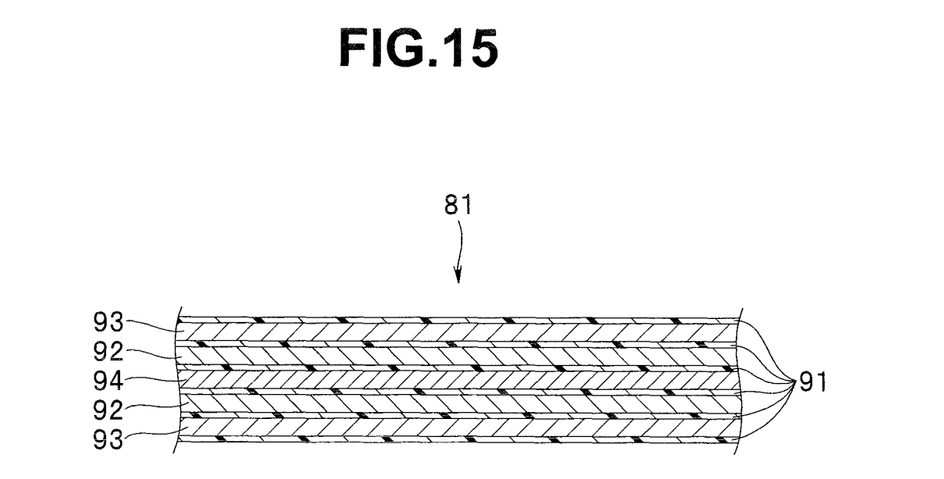
FIG. 15 is a cross-sectional view illustrating a configuration of the flexible printed board, according to the third embodiment.

FIGS. 12 to 15 relate to the third embodiment of the present invention. FIG. 12 is a view illustrating a circuit board portion formed of a flexible printed board on which various electronic parts are mounted, the printed board being expanded on a frame member. FIG. 13 is a view illustrating the circuit board portion of FIG. 12, in which the flexible printed board disposed on the frame member has been changed in shape to wrap the various electronic parts mounted on the flexible printed board. FIG. 14 is a cross-sectional view illustrating the circuit board portion disposed on the frame member, being in the state of FIG. 13. FIG. 15 is a cross-sectional view illustrating a configuration of the flexible printed board. It should be noted that, in the following description as well, components having the same configurations as those in the first and second embodiments described above are designated with the same reference symbols to omit detailed description and operational advantages of the components.

As shown in FIGS. 12 to 14, the circuit board portion 31 of the frame member 30 according to the present embodiment includes a flexible printed board (hereinafter abbreviated as "FPC") 81 on which the electronic parts explained in the first embodiment are mounted. The FPC 81 is arranged on one surface of the metal frame board 30a, with faces thereof, five here, being expanded. Of the five faces, the electronic parts are mounted on three faces, i.e. one face on the frame board 30a and two faces opposed to each other.

One of the two opposed faces on which the electronic parts are mounted, has an edge portion which is formed into a projected portion 82, and the other face has an edge portion which is formed into an engagement hole 83 for engagement with the projected portion 82. The projected portion 82 of the FPC 81 is brought into engagement first with the engagement hole 83 so that the two opposed faces can wrap the electronic parts. As a result, edge portions of two faces mounted with no electronic parts are changed in shapes to overlap with each other. As shown in FIG. 13, the two overlapped edge portions are stuck by a tape 85 so as to press with each other.

In this way, as shown in FIGS. 13 and 14, the circuit board portion 31 will have a shape of a deformed envelope, with the FPC 81 wrapping the electronic parts. Also, the FPC 81 has a lower surface provided with a connecting pattern. The connecting pattern establishes electrical connection between the frame board 30a and ground layers that will be described later, through welded portions 86 which are obtained by soldering or the like, and is fixed to one surface of the frame board 30a. Alternatively, it may be so configured that the FPC 81 is provided with through holes to electrically connect the frame board 30a with the ground layers.

As shown in FIG. 15, the FPC 81 is configured by four ground layers 92 and 93, and a signal layer 94, with each of the layers and surfaces being ensured to be insulated by insulation layers 91, similar to the first embodiment. Of the four ground layers 92 and 93, two layers that sandwich the signal layer 94 are stacked as first ground layers 92 to which shields of the coaxial lines of the composite cables 23 and 32 are connected for electrical connection, and two layers that are located on front and back surfaces are stacked as second ground layers 93 to which respective overall shields of the composite cables 23 and 32, the insertion portion 9 and the universal cable 17 are connected for electrical connection.

In the present embodiment, although the configuration for establishing electrical connection for the composite cables 23 and 32 is not shown, the frame board 30a is provided with connectors which establish electrical connection for the composite cables 23 and 32. In particular, the composite cables 23 and 32 are configured to be electrically connected to the electronic parts on the circuit board portion 31 through conductive foils printed on the frame board 30a. In addition, the coaxial line shields and the overall shields are also electrically connected to the ground layers 92 and 93 of the FPC 81 through the conductive foils printed on the frame board 30a.

The circuit board portion 31 of the present embodiment configured as described above wraps the electronic parts with the FPC 81 provided on the frame board 30a. Accordingly, the FPC 81 may have a configuration for ensuring noninterference property and tolerance against electromagnetic influences on the electronic parts. In other words, in the FPC 81, the second ground layers 93 structuring shield layers are located on the side of the surfaces of the enveloped shape. Thus, the FPC 81 configures a cover body for ensuring noninterference property and tolerance against electromagnetic influences from outside on the enclosed electronic parts.

As described above, the electronic endoscope apparatus 2 of the present embodiment uses the FPC 81 for the circuit board portion 31 arranged in the operation portion 10. Thus, there is no necessity of providing a metal cover for covering the electronic parts to ensure electromagnetic tolerance, leading to reduction in the entire height of the circuit board portion 31 and thus leading to downsizing.

Specifically, in order to maintain insulation from the covered electronic parts, the metal cover has a shape that can form a space for distancing the cover from the electronic parts by a predetermined distance. For this reason, a space for providing the metal cover has to be ensured in the operation portion 10 according to thickness (size) of the metal cover. Thus, there has been a limitation in downsizing the operation portion 10 of the electronic endoscope apparatus 2.

In this regard, in the electronic endoscope apparatus 2 of the present embodiment, the FPC 81, which can freely change shape and can also serve as a metal cover, is arranged in the operation portion 10. Therefore, the space occupied by the circuit board portion 31 in the operation portion 10 can be made small. As a result, the operation portion 10 can be downsized compared with the case where a metal cover for covering electronic parts is provided. Further, owing to the absence of the metal cover from the circuit board portion 31, there is no necessity of providing the frame board 30a with a structure for fixing the metal cover. Thus, the number of parts can be reduced to thereby improve assembling properties.

According to the present invention configured as described above, increase of size can be prevented in spite of the arrangement of an image pickup apparatus, which can acquire high-quality images, at the distal end portion of the insertion portion. In particular, the present invention can realize an electronic endoscope apparatus that can prevent increase of a diameter of the insertion portion.

The invention described above is not limited to the above embodiments, but may be variously modified for implementation within a scope not departing from the spirit of the invention. Further, since inventions of various stages are included in the embodiments, various inventions may be extracted by adequately combining a plurality of disclosed components.

For example, being removed with some components from all the components indicated in the embodiments, the configuration removed with the components may be extracted as an invention, provided the advantages as described can be obtained for the problems to be solved by the invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electronic endoscope apparatus comprising:
   an image pickup apparatus which is mounted on a distal end portion of an insertion portion;
   an operation portion which is consecutively provided at the insertion portion and at least includes bending operation means for performing a bending operation of a bending portion provided at the insertion portion;
   an electrical cable which is extended from the operation portion and connected to an external device;
   a frame member incorporated in the operation portion and configured to establish electrical connection between a shield of the insertion portion and a shield of the electrical cable; and
   a rigid board arranged parallel to the frame member in the operation portion and including a relay circuit portion which comprises various electronic parts for exchanging signals with the external device and a solid-state image pickup device of the image pickup apparatus,
   wherein the bending operation means is provided on one side of the frame member and the rigid board is provided on the other side opposite to the one side of the frame member.

2. The electronic endoscope apparatus according to claim 1, wherein:
   the insertion portion has a treatment instrument channel through which a treatment instrument is inserted, the treatment instrument channel being arranged being inserted into the insertion portion; and
   an opening portion of the treatment instrument channel is arranged in the operation portion so as to be positioned apart from a connector of the rigid board by a predetermined distance, the connector being connected to a cable extending to the solid-state image pickup device.

3. The electronic endoscope apparatus according to claim 1, wherein:
   the rigid board is arranged parallel to the circuit board portion to be apart from one surface of the frame member by a predetermined distance.

4. The electronic endoscope apparatus according to claim 2, wherein:
   the rigid board being arranged parallel to the circuit board portion to be apart from one surface of the frame member by a predetermined distance.

5. The electronic endoscope apparatus according to claim 4, wherein:
   the treatment instrument channel is connected to a side of the external device so as to communicate with a tubular body which is extended in the electrical cable; and
   the tubular body is arranged between the frame member along one side portion of the rigid board and the rigid board.

6. The electronic endoscope apparatus according to claim 1, wherein the rigid board is arranged parallel to the frame member to be apart from one surface of the frame member by a predetermined distance.

7. The electronic endoscope apparatus according to claim 1, wherein the insertion portion has a treatment instrument channel through which a treatment instrument is inserted, the treatment instrument channel being arranged being inserted into the insertion portion; and
   a opening portion of the treatment instrument channel is arranged in the operation portion so as to be positioned apart from a connector of the rigid board by a predetermined distance, the connector being connected to a cable extending to the solid-state image pickup device.

8. The electronic endoscope apparatus according to claim 7, wherein
   the rigid board is arranged parallel to the frame member to be apart from one surface of the frame member by a predetermined distance.

9. The electronic apparatus according to claim 8, wherein:
   the treatment instrument channel is connected to a side of the external device so as to communicate with a tubular body which is extended in the electrical cable; and the tubular body is arranged between the frame member along one side portion of the rigid board and the rigid board.

* * * * *